United States Patent [19]
Ikuno et al.

[11] 4,154,240
[45] May 15, 1979

[54] ELECTRIC POWER SOURCE FOR ELECTROSURGICAL APPARATUS

[75] Inventors: Yuji Ikuno, Hino; Yutaka Tanaka, Hachioji, both of Japan

[73] Assignee: Olympus Optical Co., Ltd., Tokyo, Japan

[21] Appl. No.: 866,224

[22] Filed: Jan. 3, 1978

[30] Foreign Application Priority Data

Jan. 14, 1977 [JP] Japan .................................. 52-3292

[51] Int. Cl.$^2$ ........................ A61B 17/36; A61N 3/00
[52] U.S. Cl. ........................ 128/303.14; 128/303.17; 128/422
[58] Field of Search .................... 128/303.14, 303.17, 128/303.13, 421–423

[56] References Cited
U.S. PATENT DOCUMENTS

| | | | |
|---|---|---|---|
| 3,699,967 | 10/1972 | Anderson | 128/303.14 |
| 3,804,096 | 4/1974 | Gonser | 128/303.14 |
| 3,885,569 | 5/1975 | Judson | 128/303.14 |
| 3,897,787 | 8/1975 | Ikuno et al. | 128/303.14 |
| 3,898,991 | 8/1975 | Ikuno et al. | 128/303.14 |

*Primary Examiner*—Lee S. Cohen

[57] ABSTRACT

A high frequency oscillator and a low frequency oscillator are provided to produce a high frequency cutting signal and a low frequency signal respectively. The high frequency cutting signal is modulated by a signal produced by differentiating the low frequency signal to form a coagulation signal. The high frequency cutting signal and the coagulation signal are compounded on a time division basis by a blend control signal generated by a blend control signal generating circuit to form a blend signal.

3 Claims, 7 Drawing Figures

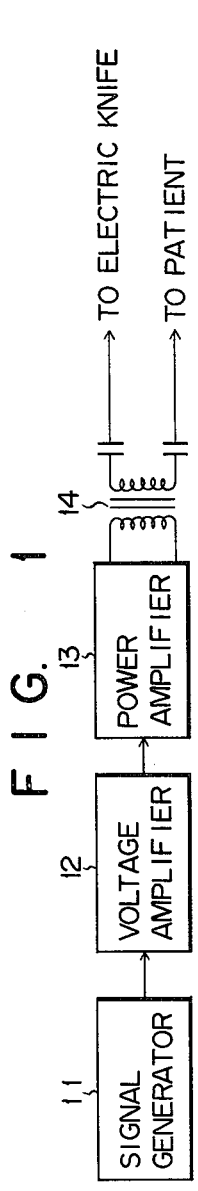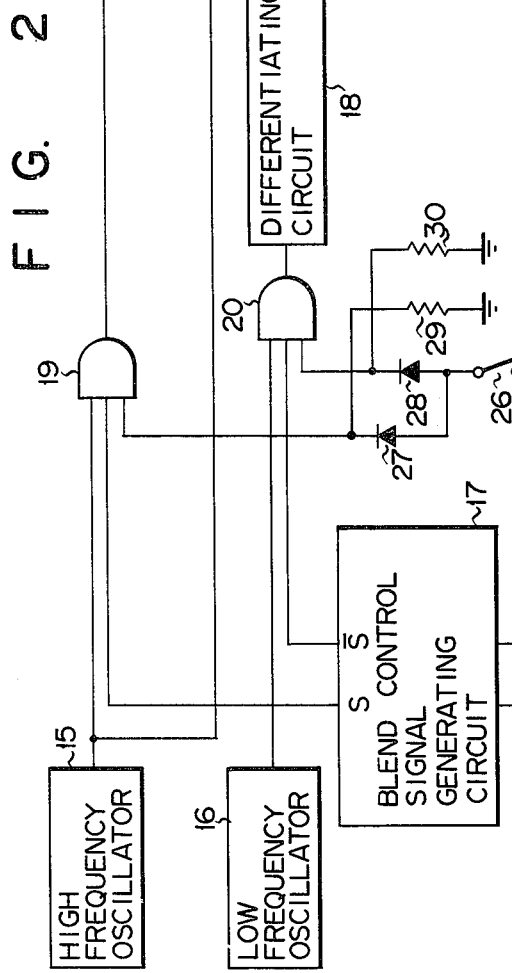

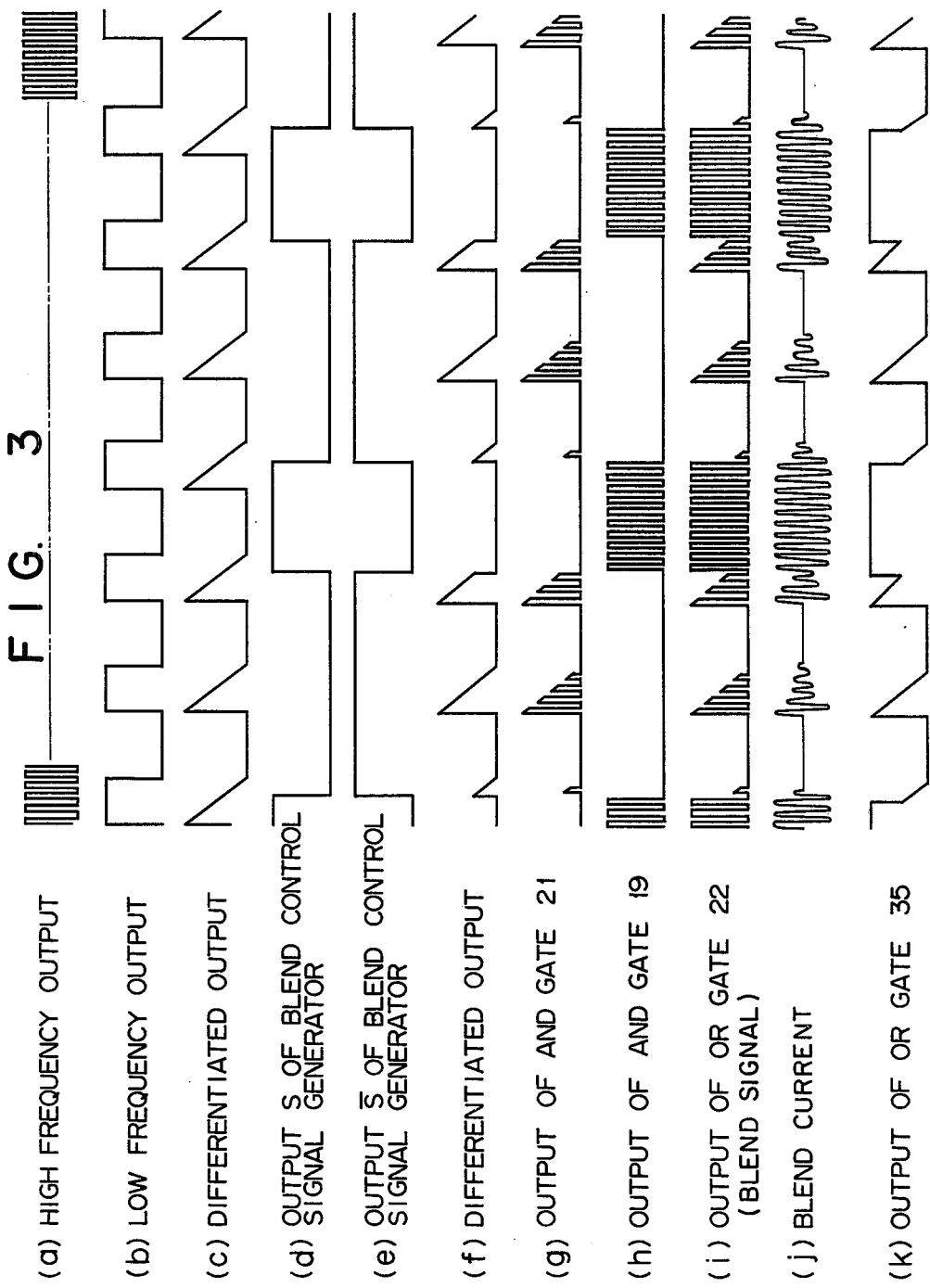

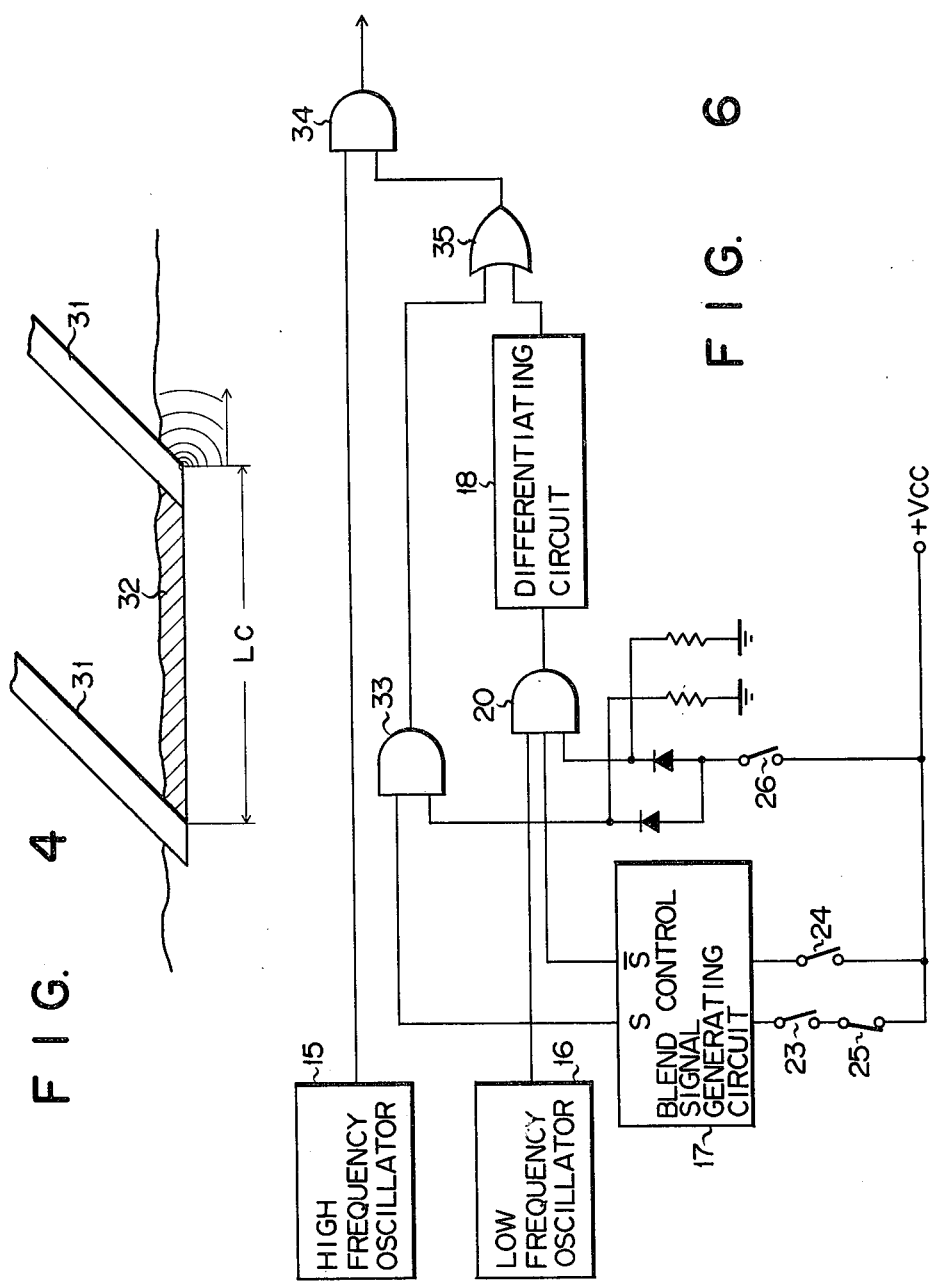

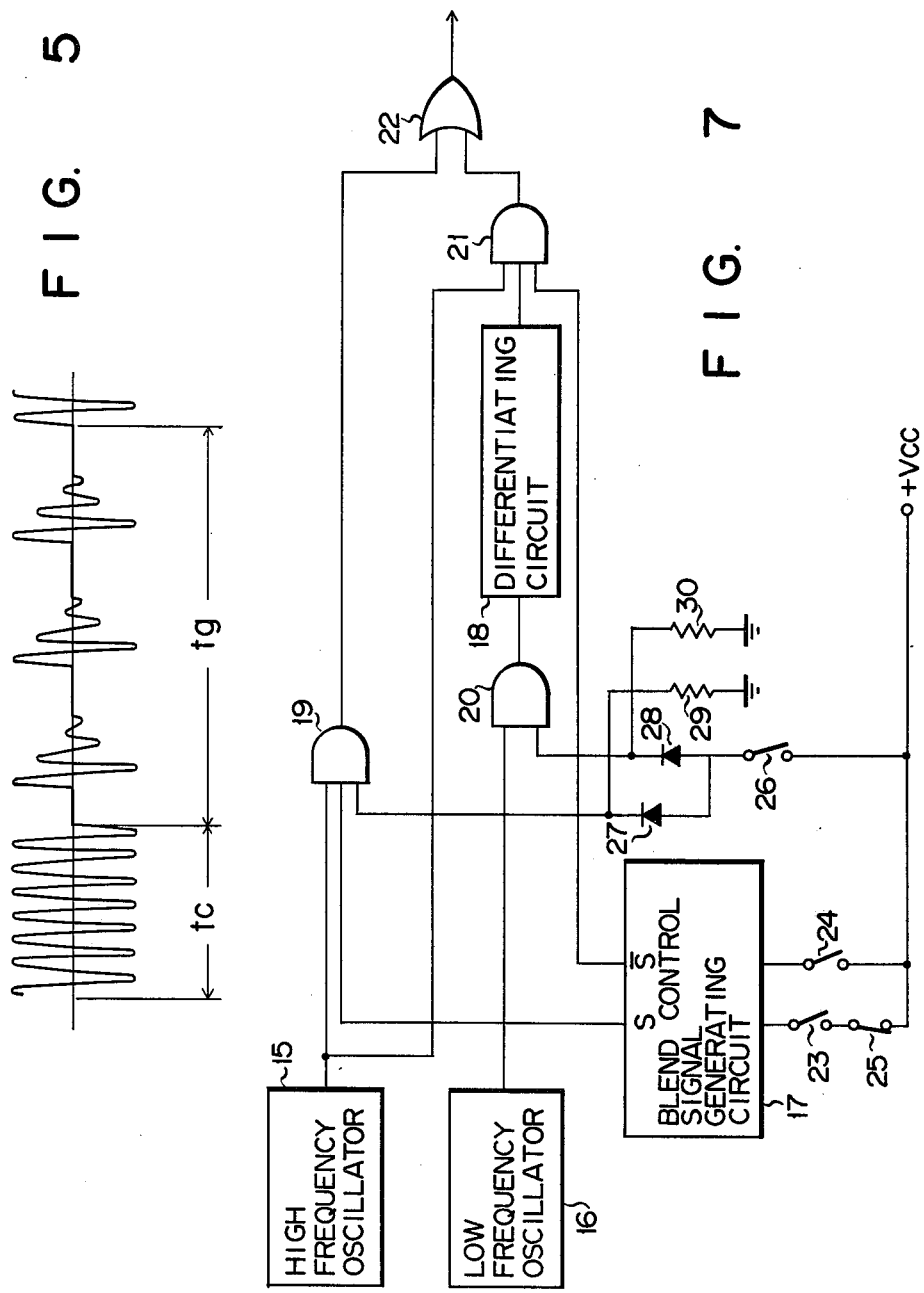

ELECTRIC POWER SOURCE FOR ELECTROSURGICAL APPARATUS

BACKGROUND OF THE INVENTION

This invention relates to an electric power source for electrosurgical apparatus which selectively generates a cutting signal, a coagulation signal and a blend signal.

An electrosurgical apparatus is generally constructed to selectively generate cutting current, coagulation current and blend current. Usually, cutting current applies stronger cutting effect to a human body than the coagulation effect caused by coagulation current. For this reason, where blend current is used the coagulation effect can be expected only when a small blend current is used. Furthermore when the blend current varies, the ratio between the cutting current and the coagulation current which are contained in the blend current varies so that stable cutting effect and coagulation effect can not be obtained.

SUMMARY OF THE INVENTION

It is an object of this invention to provide an improved electric power source for electrosurgical apparatus capable of always providing stable cutting effect and coagulation effect.

According to this invention, there is provided an electric power source for electrosurgical apparatus comprising a high frequency cutting signal generator, a low frequency signal generator, means for modulating the high frequency cutting signal with the low frequency signal for producing a coagulation signal, and means to compound the cutting signal and the coagulation signal on the time division basis for producing a blend signal.

BRIEF DESCRIPTION OF THE DRAWING

FIG. 1 is a block diagram showing one example of the electric power source for electrosurgical apparatus according to this invention;

FIG. 2 is a connection diagram showing a signal generating circuit shown in FIG. 1 and selectively generates a cutting signal, a coagulation signal and a blend signal;

FIG. 3 shows waveforms of electric signals at various portions of the circuit shown in FIG. 2;

FIG. 4 is a diagrammatic representation showing the effect of an electric knife on a biological structure;

FIG. 5 shows a waveform of a blend current;

FIG. 6 is a connection diagram showing another modification of the signal generating circuit; and FIG. 7 is a circuit diagram modified the circuit of FIG. 2.

DESCRIPTION OF THE PREFERRED EMBODIMENTS

An electrical power source for electrosurgical apparatus shown in FIG. 1 comprises a signal generating circuit 11 which is constructed to selectively generate a cutting signal, a coagulation signal and a blend signal as will be described later in more detail. The output signal of the signal generating circuit 11 is amplified by a voltage amplifier 12 and then by a power amplifier 13. The output of the power amplifier 13 is applied across an electric knife (not shown) through a transformer 14 and a body of a patient (not shown).

FIG. 2 shows the detail of the circuit construction of the signal generating circuit 11. More particularly, it comprises a high frequency oscillator 15 which generates a high frequency pulse having a frequency of 575 KHz, for example, a low frequency oscillator 16 which generates a low frequency pulse having a frequency of 5 KHz, for example, and a blend control signal generator 17 constituted by a multivibrator, for example. The output of the high frequency oscillator 15 is applied to the first inputs of AND gate circuits 19 and 21 while the output of the low frequency oscillator 16 is applied to the first input of an AND gate circuit 20. The output terminals S and $\overline{S}$ of the blend control signal generator 17 are connected to the second inputs of the AND gate circuits 19 and 20 respectively. An input terminal corresponding to the output terminal S of the blend control signal generator 17 is connected to a source $+V_{CC}$ via switches 23 and 25 which are connected in series, while an input terminal corresponding to output terminal $\overline{S}$ is connected to the source $+V_{CC}$ via a switch 24. The source $+V_{CC}$ is connected to the anode electrodes of diodes 27 and 28 via switch 26 interlocked with switches 23, 24 and 25, and the cathode electrodes of these diodes are connected to the third inputs of AND gate circuits 19 and 20 respectively and to the ground via resistors 29 and 30 respectively.

The output of the AND gate circuit 20 is connected to the second input of AND gate circuit 21 via a differentiating circuit 21 and the outputs of AND gate circuits 19 and 21 are connected to the first and second inputs of an OR gate circuit 22 having an output connected to the input of the voltage amplifier 12 shown in FIG. 1. The signal generating circuit described above operates as follows. Thus, the high frequency oscillator 15 generates a high frequency pulse signal a shown in FIG. 3 which is applied to AND gate circuits 19 and 21. The low frequency oscillator 16 generates a low frequency pulse signal b which is applied to AND gate circuit 20. Under these conditions when the blend control signal switch 25 is closed, the coagulation switch 24 is opened and the cutting signal switch 13 is closed, the output S of the blend control signal generating circuit 17 becomes a high level, whereas the output $\overline{S}$ becomes a low level. On the other hand, when the blend signal switch 25 and the coagulation signal switch 24 are closed while the cutting signal switch 23 is opened the output S of the blend control signal generating circuit 17 becomes the low level while the output $\overline{S}$ becomes the high level. When the inputs of the blend control signal generating circuit 17 corresponding to the outputs S, $\overline{S}$ are opened, the blend control signal generating circuit 17 oscillates to produce signals d and e shown in FIG. 3 on the outputs S and $\overline{S}$ respectively.

The blend control signal generating circuit 17 generates output signals in a manner as above described, and the cutting signal, the coagulation signal and blend signal are generated as follows:

(i) A case in which only the cutting signal is generated.

In this case, the cutting switch 23 and the blend switch 25 are closed while the coagulation switch 24 is opened. As a consequence, the output S of the blend signal generating circuit 17 becomes the high level. When the cutting switch 23 is closed, the switch 26 interlocked therewith is also closed. Consequently, the AND gate circuit 19 is enabled to supply the high frequency pulse signal a generated by the high frequency oscillator 15 to the voltage amplifier 12 via AND gate circuit 19, and OR gate circuit 22. The high frequency signal is amplified by the voltage amplifier 12 and the power amplifier 13 and then supplied to the electric knife as the high frequency cutting current through transformer 14.

(ii) A case wherein only the coagulation signal is generated.

In this case, the coagulation switch 24 and the blend switch 25 are closed, and the cutting switch 23 is opened with the result that the output $\overline{S}$ of the blend signal generating circuit 17 becomes the high level. At this time, the switch 26 interlocked with switch 24 is also closed. Consequently, AND gate circuit 20 is enabled to apply the low frequency signal b generated by the low frequency oscillator 16 to the differentiating circuit 18. Accordingly, the differentiating circuit 18 produces a differentiated signal c shown in FIG. 3. When this differentiated signal c and the high frequency signal a are applied to the inputs of the AND gate circuit 21, the high frequency signal a is modulated by the differentiated signal c to form the coagulation signal which is applied to the electric knife (not shown) via the OR gate circuit 22 and the amplifiers 12 and 13.

(iii) A case wherein a blend signal is produced.

In this case, switches 23, 24 and 25 which are provided for the purpose of causing the blend control signal generating circuit 17 to self-oscillate are opened. When the blend control signal generating circuit 17 oscillates, signals d and e are produced on the outputs S and $\overline{S}$ as shown in FIG. 3. Under these conditions, when cutting switch 23 is closed in order to close the switch 26, the output b of the low frequency oscillator 16 is applied to the differentiating circuit 18 via AND gate circuit 20 only when the blend control signal e is at the high level. Accordingly, the differentiating circuit 18 produces a differentiated signal f shown in FIG. 3. When this signal f is applied to the inputs of AND gate circuit 21 together with the high frequency signal a, the AND gate circuit 21 is enabled to produce an output signal g which is formed by modulating the high frequency signal a with the differentiated signal f. On the other hand, the high frequency signal a passes through the AND gate circuit 19 only when the blend control signal d is at the high level. In other words, the AND gate circuit 19 produces a signal h corresponding to the high frequency signal a modulated by the blend control signal d. When signals g and h are supplied to the inputs of the OR gate circuit 22 from AND gate circuits 19 and 21 a mixture of these signals g and h, that is a blend signal i is produced. Thus, the blend signal i corresponds to a composite signal which is formed by compounding, on a time division basis, the high frequency signal, or the cutting signal, and a signal which is formed by amplitude modulating the high frequency signal with the differentiated signal, that is, the coagulation signal. This blend signal i is supplied to the electric knife as the blend current 1 via amplifiers 12 and 13 and transformer 14. As above described, the blend current is produced by compounding the cutting current and the coagulation current on the time division basis and not by merely superposing each other these two currents so that the cutting current and the coagulation current do not interfere with each other. Accordingly, the cutting effect and the coagulation effect are manifested independently.

FIG. 4 shows the cutting and coagulation effects produced by the electric knife 31, and FIG. 5 shows the waveform of the blend current which flows for producing the cutting and coagulation effects. In FIGS. 4 and 5 during an interval $t_c$ in which the cutting current flows through the electric knife 31, the biological structure 32 is out for a length $L_C$ and then the coagulation current flows through the knife for an interval of $t_g$. Then the biological structure 32 coagulates in a direction shown by an arrow due to the heat produced by the coagulation current. As the cutting current flows again through the electric knife 31 the biological structure 32 is cut again. In this manner, the cutting knife 31 cuts the biological structure after its cut portion has been coagulated thus manifesting efficient blood stopping function.

FIG. 6 shows a modified blend control signal generating circuit 11 in which the high frequency signal generated by the high frequency oscillator 15 is applied to one input of an AND gate circuit 34, whereas to the input of an AND gate circuit 33 are applied the output S of the blend control signal generating circuit 17 and the voltage of the source $+V_{CC}$ which is supplied through switch 26. The outputs of the AND gate circuit 33 and the differentiating circuit 18 are applied to the inputs of an OR gate circuit 35, and the output thereof is applied to the second input of the AND gate circuit 34. The other circuit construction is the same as that of the circuit shown in FIG. 2. In the modification shown in FIG. 6, the differentiated signal f produced by the differentiating circuit 18 and the blend control signal d passing through the AND gate circuit 33 are compounded by the OR gate circuit 35 to produce signal k by the AND gate circuit 34. The high frequency signal a produced by the high frequency oscillator 15 is modulated by this signal k by AND gate circuit 34 to produce a blend signal i. As above described, the circuit shown in FIG. 6 functions in the same manner as that shown in FIG. 2.

As above described, according to this invention a cutting signal is produced by a high frequency oscillator and the cutting signal is modulated by a low frequency differentiated signal which is formed by differentiating a low frequency signal produced by a low frequency oscillator to form a coagulation signal. The cutting signal and the coagulation signal are compounded on a time division basis to produce a blend signal. Accordingly, a blend current based on the blend signal thus formed manifests stable cutting effect and coagulation effect whereby efficient blood stopping function can be obtained.

Although the invention has been shown and described in terms of some preferred embodiments thereof it is clear that many changes and modifications will be obvious to one skilled in the art without departing from the scope of the invention. For example, in the embodiment shown in FIG. 2, the output $\overline{S}$ of the blend control signal generating circuit 17 may be the connected to one input of AND gate circuit 21 instead of AND gate circuit 20, as shown in FIG. 7.

What we claim is:

1. An electric power source for electrosurgical apparatus comprising a high frequency oscillator for generating a high frequency cutting signal; a low frequency oscillator for generating a low frequency signal; a blend control signal generating circuit including means for generating two blend control signals having opposite phases; a first AND gate circuit operatively connected to said high frequency oscillator to receive said high frequency cutting signal therefrom and operatively connected to said generating circuit to receive one of said blend control signals for producing a signal corresponding to a logical product of said cutting signal and said one blend control signal; a second AND gate circuit operatively connected to at least said low frequency oscillator and said generating circuit to receive respectively therefrom said low frequency signal and the other blend control signal, for producing a signal corresponding to a logical product thereof; a differentiating circuit operatively connected to the output of said second AND gate circuit for differentiating the output signal of said second AND gate circuit and having an output; a third AND gate circuit operatively connected to said high frequency oscillator for receiving said high frequency cutting signal and to the output of said differentiating circuit for producing a coagulation signal corresponding to a logical product thereof; and an OR gate circuit respectively operatively connected to said first AND gate circuit and said third AND gate circuit for receiving the signal of said first and third AND gate circuits, and having an output to thereby output a blend signal when the blend control signal generating circuit generates the signals having opposite phases.

2. An electric power source for electrosurgical apparatus according to claim 1 which further includes means for amplifying the output signal from said OR gate circuit and transformer means for transforming the amplified signal from said amplifying means.

3. An electric power source of electrosurgical apparatus comprising a high frequency oscillator for producing a high frequency cutting signal; a low frequency oscillator for producing a low frequency signal; a blend control signal generating circuit including means for producing first and second blend control signals having opposite phases; a first AND gate circuit operatively connected to at least said low frequency oscillator and to said generating circuit for receiving said low frequency signal and said first blend control signal for passing said low frequency signal when said first blend control signal is at a high level; a differentiating circuit operatively connected to said first AND gate circuit for differentiating the output signal of said first AND gate circuit and having an output; an OR gate circuit operatively connected to the output of said differentiating circuit and operatively connected to said generating circuit for receiving said second blend control signal and having an output; and a second AND gate circuit operatively connected to said high frequency oscillator for receiving said high frequency cutting signal and operatively connected to the output of said OR gate circuit.

* * * * *